United States Patent

Ainsworth et al.

Patent Number: 4,596,800
Date of Patent: Jun. 24, 1986

[54] HYDROXYMORPHOLINE DERIVATIVES

[75] Inventors: Anthony T. Ainsworth, Bishop's Stortford; Richard M. Hindley, Reigate, both of England

[73] Assignee: Beecham Group p.l.c., England

[21] Appl. No.: 756,795

[22] Filed: Jul. 19, 1985

[30] Foreign Application Priority Data

Jul. 21, 1984 [GB] United Kingdom ............... 8418657

[51] Int. Cl.⁴ .................. A61K 31/535; C07D 265/30
[52] U.S. Cl. ..................................... 514/233; 514/234; 514/236; 514/237; 514/239; 514/240; 544/105; 544/130; 544/141; 544/162; 544/168; 544/169; 544/171; 544/172; 544/174; 560/39; 560/42; 562/444; 562/448; 562/451; 564/156; 564/165; 564/344
[58] Field of Search ............... 544/105, 130, 141, 162, 544/168, 169, 171, 172, 174; 514/233, 234, 236, 237, 239, 240

[56] References Cited

U.S. PATENT DOCUMENTS 3,225,042 12/1965 Dillard et al. ............... 544/105 X
4,360,519 11/1982 White et al. ............... 544/174 X

FOREIGN PATENT DOCUMENTS 140359 5/1985 European Pat. Off. .

Primary Examiner—Richard L. Raymond
Attorney, Agent, or Firm—Hopgood, Calimafde, Kalil, Blaustein & Judlowe

[57] ABSTRACT

A compound of formula (I)

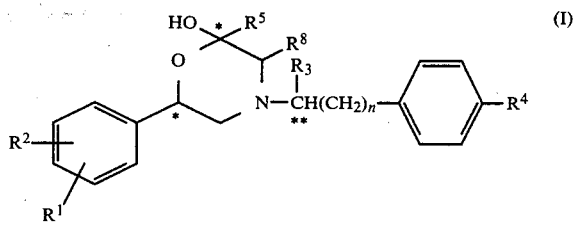

or a pharmaceutically acceptable salt thereof, in which
R¹ is hydrogen, halogen, or trifluoromethyl;
R² is hydrogen or halogen;
R³ is hydrogen or methyl;
R⁴ is —O(CH₂)ₐCO₂H or an ester or amide derivative thereof, O(CH₂)ᵦM or —CO₂H or an ester or amide derivative thereof wherein
a is an integer from 1 to 6,
b is an integer from 2 to 7, and
M is hydroxy, C₁₋₆ alkoxy or

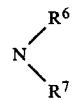

wherein
R⁶ and R⁷ are each hydrogen or C₁₋₆ alkyl or

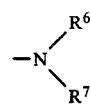

together form a five or six membered ring;
R⁵ is C₁₋₆ alkyl; C₁₋₆ alkyl substituted by carboxy or esters and amides thereof; or phenyl optionally substituted by C₁₋₆ alkyl, halogen, alkoxy or trifluoromethyl;
R⁸ is hydrogen or C₁₋₆ alkyl or R⁸ together with R⁵ form a carbocyclic ring; and
n is 1 or 2.

Processes for preparing these compounds and their use in therapy is also described.

7 Claims, No Drawings

HYDROXYMORPHOLINE DERIVATIVES

The present invention relates to hydroxymorpholine derivatives which have anti-hyperglycaemic and/or anti-obesity activity, to processes for their production and to their use in medicine.

European Published patent application No. 0140359 describes compounds of formula (A)

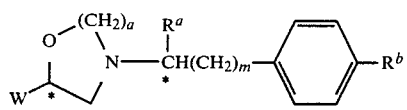

or a salt thereof, in which

W is phenyl optionally substituted by halogen or trifluoromethyl, or a benzofuran-2-yl group, $R^a$ is hydrogen or methyl, $R^b$ is carboxyl or a group O-Z-CO$_2$H or an ester or amide thereof; a group O-E-NR$^c$R$^d$ or a group O-E-OR$^e$, wherein $R^c$, $R^d$ and $R^e$ each represents hydrogen or $C_{1-6}$ alkyl, Z is a $C_{1-6}$ straight or branched alkylene chain, m is 1 or 2, q is 2 or 3, and E is a $C_{2-7}$ straight or branched alkylene chain with at least two carbon atoms separating the two heteroatoms in the group R$^2$. These compounds are described as having anti-hyperglycaemic and/or anti-obesity activity.

The applicants have now discovered a class of novel hydroxy morpholine derivatives which have anti-hyperglycaemic and/or anti-obesity activities.

According to the present invention there is provided a compound of formula (I):

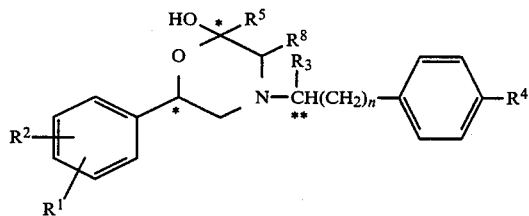

or a pharmaceutically acceptable salt thereof, in which $R^1$ is hydrogen, halogen, or trifluoromethyl;

$R^2$ is hydrogen or halogen;

$R^3$ is hydrogen or methyl;

$R^4$ is —O(CH$_2$)$_a$ CO$_2$H or an ester or amide derivative thereof, O(CH$_2$)$_b$M or —CO$_2$H or an ester or amide derivative thereof wherein a is an integer from 1 to 6, b is an integer from 2 to 7, and M is hydroxy, $C_{1-6}$ alkoxy or

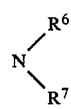

wherein $R^6$ and $R^7$ are each hydrogen or $C_{1-6}$ alkyl or

together form a five or six membered ring;

$R^5$ is $C_{1-6}$ alkyl; $C_{1-6}$ alkyl substituted by carboxy or esters and amides thereof; or phenyl optionally substituted by $C_{1-6}$ alkyl, halogen, alkoxy or trifluoromethyl;

$R^8$ is hydrogen or $C_{1-6}$ alkyl or $R^8$ together with $R^5$ form a carbocyclic ring; and n is 1 or 2.

Suitably $R^1$ is hydrogen, chlorine or trifluoromethyl.

Preferably, $R^1$ is in the meta-position.

Suitably $R^2$ is hydrogen.

Preferably $R^3$ is methyl.

Suitably $R^4$ is —O(CH$_2$)$_a$CO$_2$H or an ester thereof, or —CO$_2$H or an ester thereof.

Suitable amide derivatives for the $R^4$ group are CONR$^6$R$^7$ or —O(CH$_2$)$_a$CONR$^6$R$^7$, wherein $R^6$ and $R^7$ are as defined in relation to formula (I).

Suitable esters of the group $R^4$ are $C_{1-6}$ alkyl esters such as methyl and ethyl esters, preferably the methyl ester.

Suitably $R^5$ is methyl, carboethoxymethyl or phenyl.

Suitably $R^8$ is hydrogen or methyl.

Suitably $R^5$ and $R^8$ together form a 5 or 6 membered carbocyclic ring.

Preferably a is 1.

Suitably b is 2.

Preferably n is 1.

Pharmaceutically acceptable salts of compounds of formula (I) include acid addition salts formed with a pharmaceutically acceptable acid such as hydrochloric acid, hydrobromic acid, orthophosphoric acid, sulphuric acid, methane sulphonic acid, toluenesulphonic acid, acetic acid, propionic acid, lactic acid, citric acid, fumaric acid, malic acid, succinic acid, salicylic acid or acetylsalicylic acid.

Other pharmaceutically acceptable salts of the compounds of formula (I) include metal salts, such as for example aluminum, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine or quinoline.

Compounds of formula (I) always have two asymmetric carbon atoms, marked with asterisks in the formula. In addition when $R^3$ is methyl, the carbon atom marked ** will also be asymmetric, giving rise to eight stereoisomeric forms. The present invention encompasses all stereoisomers of the compounds of formula (I) whether free from other stereoisomers or admixed with other stereoisomers in any proportion and thus includes, for instance, racemic mixtures of enantiomers.

The absolute configuration of any compound of formula (I) may be determined by conventional X-ray crystallographic techniques.

Examples of compounds of formula (I) include:

4-[2-(4-(6-(3-Chlorophenyl)-2-hydroxy-2-phenyl)morpholinyl)propyl]phenoxyacetic acid;
4-[2-(4-(2,6-Diphenyl-2-hydroxy)morpholinyl)propyl]benzoic acid;
4-[2-(4-(6-(3-Chlorophenyl)-2-hydroxy-2-methyl)morpholinyl)propyl]phenoxyacetic acid;
4-[2-(4-(6-(3-Chlorphenyl)-2-carboethoxymethyl-2-hydroxy)morpholinyl)propyl]phenoxyacetic acid;
4-[2-(4-(6-(3-Trifluoromethylphenyl)-2-hydroxy-2-phenyl)morpholinyl)propyl]phenoxyacetic acid;
4-[2-(4-(2-hydroxy-2-methyl-6-phenyl)morpholinyl)propyl]benzoic acid;
4-[2-(4-(6-(3-Chlorophenyl)-2,3-dimethyl-2-hydroxy)morpholinyl)propyl]phenoxyacetic acid;
4-[2-(4-(2-(3-Chlorophenyl)-9-hydroxy-5,6,7,8-tetrahydrobenz-(1,4)-oxazinylpropyl]phenoxyacetic acid;
and ester or amide derivatives thereof or pharmaceutically acceptable salts thereof.

The present invention also provides a process for preparing a compound of formula (I) or a salt, thereof, which process comprises cyclising a compound of formula (II)

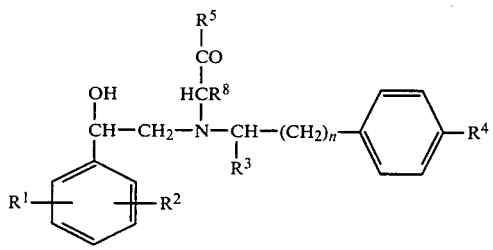

in which $R^1$, $R^2$, $R^3$, $R^4$, $R^5$, $R^8$ and n are as defined in relation to formula (I) and thereafter if desired forming a salt thereof.

The reaction may suitably be carried out in an organic solvent, preferably butanone, at elevated temperature, preferably under reflux in the presence of a base such as potassium carbonate.

The compounds of formula (II) and salts thereof are novel and as such form part of the present invention. Compounds of formula (II) can be prepared by reacting a compound of formula (III)

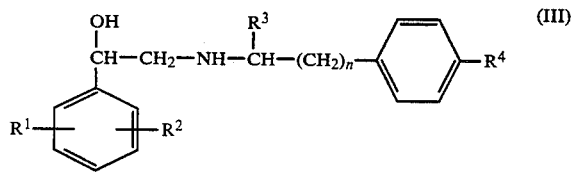

in which $R^1$, $R^2$, $R^3$, $R^4$ and n are as defined in relation to formula (I), with a compound of formula (IV)

in which $R^5$ and $R^8$ are as defined in relation to formula (I) and X is halogen, preferably chlorine or bromine.

The reaction between a compound of formula (III) and a compound of formula (IV) is suitably carried out under similar conditions to those described above for the cyclisation of the compound of formula (II). Preferably the compound of formula (II) is not isolated but is converted to the compound of formula (I) in situ.

Further according to the present invention there is provided a process for the preparation of a compound of formula (I) or a salt thereof, which process comprises reacting a compound of formula (V)

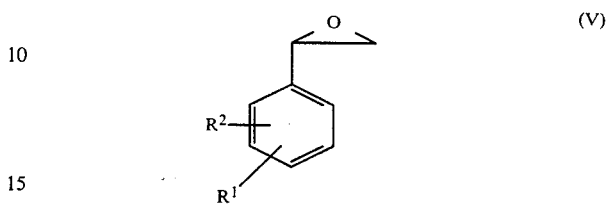

with a compound of formula (VI)

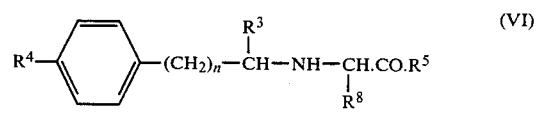

in which $R^1$, $R^2$, $R^3$, $R^4$, $R^5$, $R^8$ and n are as defined in formula (I), and thereafter if desired forming a salt thereof.

The reaction may be carried out in any suitable organic solvent, such as a $C_{1-4}$ alkanol or dimethyl sulphoxide, preferably at an elevated temperature.

Salts of compounds of formula (I) may be produced by treating a compound of formula (I) with an appropriate acid, and may be recovered by conventional methods.

Compounds of formulae (III), (IV), (V) and (VI) are either known compounds or can be prepared from known compounds by known processes or processes analogous to known processes.

Compounds of formula (I) may be separated into diastereoisomeric pairs of enantiomers by, for example, fractional crystallisation from a suitable solvent such as methanol or ethyl acetate or a mixture thereof. The pair of enantiomers thus obtained may be separated into individual stereoisomers by conventional means such as by the use of an optically active acid as a resolving agent.

Suitable optically active acids which may be used as resolving agents are described in 'Topics in Stereochemistry', Vol. 6, Wiley Interscience, 1971, Allinger, N. L. and Eliel, W. L. Eds.

Alternatively any enantiomer of a compound of formula (I) may be obtained by stereospecific synthesis using an optically pure starting material of known configuration.

A compound of formula (I) or a pharmaceutically acceptable salt, thereof (hereinafter 'the drug') may be administered as the pure drug, however, it is preferred that the drug be administered as a pharmaceutical composition also comprising a pharmaceutically acceptable carrier.

Accordingly, the present invention also provides a pharmaceutical composition comprising a compound of formula (I) or a pharmaceutically acceptable salt, thereof in combination with a pharmaceutically acceptable carrier.

As used herein the terms 'pharmaceutical composition' and 'pharmaceutically acceptable' embrace compositions and ingredients for both human and veterinary use.

uents in formula (I) are as shown in the following table:

| Example | $R^1$ | $R^2$ | $R^3$ | $R^4$ | $R^5$ | $R^8$ | n | Salt |
|---------|-------|-------|-------|-------|-------|-------|---|------|
| 1 | 3-Cl | H | $CH_3$ | $OCH_2CO_2CH_3$ | Phenyl | H | 1 | HCl |
| 2 | H | H | $CH_3$ | $CO_2CH_3$ | Phenyl | H | 1 | HCl |
| 3 | 3-Cl | H | $CH_3$ | $OCH_2CO_2CH_3$ | $CH_3$ | H | 1 | HCl |
| 4 | 3-Cl | H | $CH_3$ | $OCH_2CO_2CH_3$ | $CH_2CO_2CH_3$ | H | 1 | HCl |
| 5 | 3-$CF_3$ | H | $CH_3$ | $OCH_2CO_2CH_3$ | Phenyl | H | 1 | HCl |
| 6 | H | H | $CH_3$ | $CO_2CH_3$ | $CH_3$ | H | 1 | HCl |
| 7 | 3-Cl | H | $CH_3$ | $OCH_2CO_2CH_3$ | $CH_3$ | $CH_3$ | 1 | HCl |
| 8 | 3-Cl | H | $CH_3$ | $OCH_2CO_2CH_3$ | tetrahydro-benzo | | 1 | HCl |

Usually the compositions of the present invention will be adapted for oral administration although compositions for administration by other routes, such as by injection are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or the like.

Typical carriers may, therefore, comprise such agents as microcrystalline cellulose, starch, sodium starch glycollate, polyvinylpyrrolidone, polyvinylpolypyrrolidone, magnesium stearate, sodium lauryl sulphate, sucrose and the like.

Most suitably the composition will be provided in unit dose form. Such unit doses will normally comprise 0.1 to 1000 mg of the drug, more usually 0.1 to 500 mg and favourably 0.1 to 250 mg.

The present invention further provides a method for treating hyperglycaemia in human or non-human animals which method comprises administering an effective, non-toxic amount of a compound of formula (I) or a pharmaceutically acceptable salt thereof to a hyperglycaemic human or non-human animal.

The present invention further provides a method for treating obesity in human or non-human animals, which method comprises administering an effective, non-toxic amount of a compound of formula (I) or a pharmaceutically acceptable salt thereof to an obese human or non-human animals.

Yet further according to the present invention there is provided a compound of formula (I) as hereinbefore defined or a pharmaceutically acceptable salt thereof for use in therapy.

In particular there is provided a compound of formula (I) as hereinbefore defined or a pharmaceutically acceptable salt thereof for use in the treatment of obesity or hypoglycaemia.

In treating hyperglycaemic or obese humans the drug may be taken in doses, such as those described above, one to six times a day in a manner such as that the total daily dose for a 70 kg adult will generally be about 0.1 to 6000 mg, and more usually about 1 to 1500 mg.

In treating hyperglycaemic or obese animals, especially dogs, the drug may be administered by mouth, usually once or twice a day and at about 0.025 mg/kg to 25 mg/kg, for example 0.1 mg/kg to 20 mg/kg.

No toxicological effects would be expected at the above mentioned dosage levels.

The invention will now be illustrated with reference to the following Examples. In the Examples, the substit-

EXAMPLE 1

(RR,SS)-4-[2-(4-(6-(3-Chlorophenyl)-2-hydroxy-2-phenyl)morpholinyl)propyl]phenoxyacetic acid methyl ester hydrochloride monohydrate α-Bromoacetophenone (2.0 g) was added to a suspension of (RR,SS)-N-[2-(4-carbomethoxymethoxyphenyl)-1-methylethyl]-2-hydroxy-2-(3-chlorophenyl-)ethanamine hydrobromide (4.59 g), anhydrous potassium carbonate (5 g) and potassium iodide (5 g) in butan-2-one (100 ml). The mixture was boiled under reflux with stirring for 18 hours, α-bromoacetophenone (2 g) was added and boiling was continued for a further 2 hours. The mixture was filtered and the solvent removed under vacuum. The residue was chromatographed on silica-gel in dichloromethane to give an oil which on treatment with a solution of ethereal hydrogen chloride gave the title compound, m.p. 90°-92° C., after crystallisation from dichloromethane-diethyl ether.

$^1$H nmr δ(DMSO-$d_6$)

1.10 (3H, d); 2.5-3.75 (10H, complex); 3.65 (3H, s); 4.7 (2H, s); 5.45-5.75 (1H, complex); 6.85 (2H, d); 7.2 (2H, d); 7.4-7.9 (9H, complex); 10.4-10.7 (1H, broad s, exchanges with $D_2O$).

$^{13}$C nmr δ(DMSO-$d_6$)

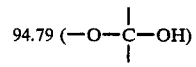

EXAMPLE 2

(RR,SS)-4-[2-(4-(2,6-Diphenyl-2-hydroxy)morpholinyl)propyl]benzoic acid methyl ester hydrochloride monohydrate The title compound, m.p. 121°-24° C. (ethyl acetate-diethyl ether-hexane) was prepared from (RR,SS)-N-[2-(4-carbomethoxyphenyl)-2-methylethyl]-2-hydroxy-2-phenylethanamine hemifumarate in a similar manner to that described in Example 1.

$^1$H nmr δ(DMSO-$d_6$)

1.15 (3H, d); 2.75-4.2 (10H, complex); 3.75 (3H, s); 5.5-5.9 (1H, d); 7.0-8.0 (14H, complex); 10.8-11.5 (1H, broad s, exchanges with $D_2O$).

$^{13}$C nmr δ(DMSO-$d_6$)

94.57 (—O—C(=O)—OH) 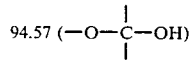

EXAMPLE 3

(RR,SS)
4-[2-(4-(6-(3-Chlorophenyl)-2-hydroxy-2-methyl)morpholinyl)propyl]phenoxyacetic acid methyl ester hydrochloride The title compound, m.p. 177°–179° C. (dichloromethane) was prepared from (RR,SS) N-[2-(4-carbomethoxymethoxyphenyl)-1-methylethyl]-2-hydroxy-2-(3-chlorophenyl)ethanamine hydrobromide and chloroacetone in a similar manner to that described in Example 1.

$^1$H nmr δ(DMSO-d$_6$)
1.10 (3H, d); 1.50 (3H, s); 2.55–3.8 (8H, complex); 3.70 (3H, s); 4.75 (2H, s); 5.25–5.5 (1H, d); 6.85 (2H, d); 7.2 (2H, d); 7.3–7.55 (4H, complex); 10.5–10.8 (1H, broad s, exchanges with D$_2$O).

$^{13}$C nmr δ(DMSO-d$_6$)

93.47 (—O—C(=O)—OH) 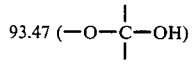

EXAMPLE 4

(RR,SS)
4-[2-(4-(6-(3-Chlorophenyl)-2-carboethoxymethyl-2-hydroxy)morpholinyl)propyl]phenoxyacetic acid methyl ester hydrochloride The title compound, m.p. 150°–152° C. (methanol-diethyl ether) was prepared from (RR,SS) N-[2-(4-carbomethoxymethoxyphenyl)-1-methylethyl]-2-(3-chlorophenyl)-2-hydroxyethanamine hydrobromide and ethyl 4-chloroacetoacetate in a similar manner to that described in Example 1.

$^1$H nmr δ(DMSO-d$_6$)
1.10 (3H, d); 1.20 (3H, t); 2.55–3.8 (10H, complex); 3.70 (3H, s); 4.05–4.2 (2H, complex); 4.75 (2H, s); 5.4 (1H, d); 6.9 (2H, d); 7.2 (2H, d); 7.45–7.6 (4H, complex); 10.4–10.6 (1H, broad s, exchanges with D$_2$O).

$^{13}$C nmr δ(DMSO-d$_6$)

93.36 (—O—C(=O)—OH) 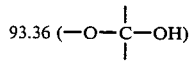

EXAMPLE 5

4-[2-(4-(6-(3-Trifluoromethylphenyl)-2-hydroxy-2-phenyl)morpholinyl)propyl]phenoxyacetic acid methyl ester hydrochloride monohydrate The title compound, m.p. 100°–104° C. (dichloromethane-diethyl ether) was prepared from N-[2-(4-carbomethoxymethoxyphenyl)-1-methylethyl]-2-hydroxy-2-(3-trifluoromethylphenyl)ethanamine in a similar manner to that described in Example 1.

$^1$H nmr δ(DMSO-d$_6$)
1.10 (3H, d); 2.7–2.8 (1H, t); 3.2–3.8 (9H, complex); 3.65 (3H, s); 4.8 (2H, s); 5.7–5.8 (1H, d); 6.9 (2H, d); 7.2 (2H, d); 7.35–8.0 (9H, complex); 10.5–10.7 (1H, broad s, exchanges with D$_2$O).

$^{13}$C nmr δ(DMSO-d$_6$)

95.25 (—O—C(=O)—OH) 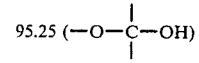

EXAMPLE 6

(RR,SS)-4-[2-(4-(2-hydroxy-2-methyl-6-phenyl)morpholinyl)-propyl]benzoic acid methyl ester hydrochloride The title compound, m.p. 173°–6° C. (diethylether-dichloromethane), was prepared from (RR,SS)-N-[2-(4-carbomethoxyphenyl)-2-methylethyl]-2-hydroxy-2-phenylethanamine hemifumarate and chloroacetone in a similar manner to that described in Example 1.

$^1$H nmr δ(DMSO-d$_6$)
1.10 (3H, d); 1.50 (3H, s); 2.55–4.0 (8H, complex); 3.85 (3H, s); 5.4 (1H, d); 7.2–7.55 (7H, complex); 7.9 (2H, d); 10.5–11.0 (1H, broad s, exchanges with D$_2$O).

EXAMPLE 7

(RR,SS)
4-[2-(4-(6-(3-Chlorophenyl)-2,3-dimethyl-2-hydroxy)-morpholinyl)propyl]phenoxyacetic acid methyl ester hydrochloride sesquihydrate The title compound, m.p. 157°–61° C. (dichloromethane) was prepared from (RR,SS) N-[2-(4-carbomethoxymethoxyphenyl)-1-methylethyl]-2-hydroxy-2-(3-chlorophenyl)ethanamine hydrobromide and 3-bromobutan-2-one in a similar manner to that described in Example 1.

$^1$H nmr δ(DMSO-d$_6$+D$_2$O).
1.10 (3H, d); 1.25–1.55 (6H, broad s); 2.5–4.2 (7H, complex); 3.70 (3H, s); 4.7 (2H, s); 5.2–5.5 (1H, d); 6.85 (2H, d); 7.2 (2H, d); 7.25–7.55 (4H, complex).

EXAMPLE 8

(RR,SS)
4-[2-(4-(2-(3-Chlorophenyl)-9-hydroxy-5,6,7,8-tetrahydrobenz-(1,4)-oxazinyl)propyl]phenoxyacetic acid methyl ester hydrochloride sesquihydrate The title compound, m.p. 173°–174° C. (dichloromethane-diethyl ether) was prepared from (RR,SS) N-[2-(4-carbomethoxymethoxyphenyl)-2-methylethyl]-2-hydroxy-2-(3-chlorophenyl)ethanamine hydrobromide and 2-chlorocyclohexanone in a similar manner to that described in Example 1.

$^1$H nmr δ(DMSO)
1.15 (3H, d); 1.3–2.2 (9H, complex); 2.65 (1H, t); 3.0–3.25 (2H, complex); 3.6–3.8 (5H, complex); 4.75 (2H, s); 5.4 (1H, d); 6.9 (2H, d); 7.2 (2H, d); 7.4–7.6 (4H, complex).

DEMONSTRATION OF EFFECTIVENESS OF COMPOUNDS (a) Anti-hyperglycaemic activity

Female CFLP mice, weighing approximately 25 g, were fasted for 24 hours prior to the study. The compounds under study were administered orally as an aqueous solution to each of 6 mice. 30 minutes later a blood sample (10 μl) was obtained from the tail for the analysis of blood glucose. Immediately after taking this blood sample, glucose (1 g/Kg body weight) was administered subcutaneously to each mouse. 6 mice were given water as a control. Blood samples were then obtained from each mouse at 30 minute intervals for 120 minutes.

Compounds that produced a significant (P<0.05) reduction of blood glucose, compared with control mice given water, at any time interval, were considered active. The area under the blood glucose curve over the 2 hour period after the administration of the glucose was calculated for each compound and compared with the value for control animals.

| Example No. | Dose $\mu$mol kg$^{-1}$ | % Reduction in Area under Blood Glucose Curve |
|---|---|---|
| 1 | 0.2 | 39 |
| 2 | 2.5 | 18 |
| 3 | 0.1 | 39 |
| 4 | 1.0 | 45 |
| 5 | 1.0 | 46 |
| 6 | 10 | 35 |
| 7 | 2.5 | 41 |
| 8 | 0.1 | 36 |

(b) Effect on Energy Expenditure

The effect of the compounds on the energy expenditure of mice was demonstrated by means of the following procedure:

Female CFLP mice, each weighing approximately 24 g were given food and water ad lib before and during the experiment. The compounds were dissolved in water by addition of one mole of hydrochloric acid per mole of compound and these solutions were administered orally to each of 12 mice. A further 12 mice were dosed orally with water. The mice were placed in boxes through which air was drawn and the oxygen content of the air leaving the boxes was measured. The energy expenditure of the mice was calculated for 3 hours after dosing from the volume of air leaving the boxes and its oxygen content, following the principles described by J. B. de V. Weir, J. Physiol. (London), 109, 1–9 (1949).

| Example No. | Dose mg. kg$^{-1}$ | Mean Energy Expenditure 0–3 h |
|---|---|---|
| 1 | 27.5 | 141 |
| 2 | 23.4 | 135 |
| 3 | 23.5 | 150 |
| 4 | 27.1 | 121 |
| 5 | 29.2 | 122 |
| 6 | 20.3 | 128 |
| 7 | — | — |
| 8 | 26.0 | 131 |

We claim:
1. A compound of formula (I)

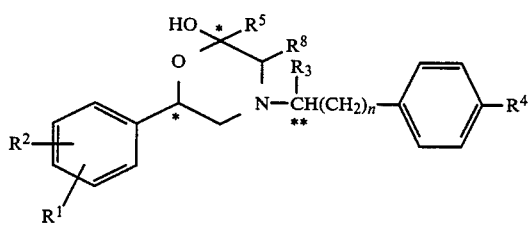

or a pharmaceutically acceptable salt thereof, in which $R^1$ is hydrogen, halogen, or trifluoromethyl;
$R^2$ is hydrogen or halogen;
$R^3$ is hydrogen or methyl;
$R^4$ is $-O(CH_2)_a CO_2H$ or an ester or amide derivative thereof, $O(CH_2)_b M$ or $-CO_2H$ or an ester or amide derivative thereof
wherein
a is an integer from 1 to 6,
b is an integer from 2 to 7, and
M is hydroxy, $C_{1-6}$ alkoxy or

wherein
$R^6$ and $R^7$ are each hydrogen or $C_{1-6}$ alkyl or

together form a five or six membered ring;
$R^5$ is $C_{1-6}$ alkyl; $C_{1-6}$ alkyl substituted by carboxy or esters and amides thereof; or phenyl optionally substituted by $C_{1-6}$ alkyl, halogen, alkoxy or trifluoromethyl;
$R^8$ is hydrogen or $C_{1-6}$ alkyl or $R^8$ together with $R^5$ form a carbocyclic ring; and
n is 1 or 2.

2. A compound according to claim 1 wherein $R_4$ is $-O(CH_2)_a CO_2H$, or a $C_{1-6}$ alkyl ester thereof or $-CO_2H$ or $C_{1-6}$ alkyl ester thereof.

3. A compound according to claim 1 wherein $R^1$ is meta-chloro or meta-trifluoromethyl.

4. A compound selected from
4-[2-(4-(6-(3-Chlorophenyl)-2-hydroxy-2-phenyl)morpholinyl)propyl]phenoxyacetic acid;
4-[2-(4-(2,6-Diphenyl-2-hydroxy)morpholinyl)propyl] benzoic acid;
4-[2-(4-(6-(-(3-Chlorophenyl)-2-hydroxy-2-methyl)morpholinyl)propyl]phenoxyacetic acid;
4-[2-(4-(6-(3-Chlorophenyl)-2-carboethoxymethyl-2-hydroxy)morpholinyl)propyl]phenoxyacetic acid;
4-[2-(4-(6-(3-Trifluoromethylphenyl)-2-hydroxy-2-phenyl)morpholinyl)propyl]phenoxyacetic acid;
4-[2-(4-(2-hydroxy-2-methyl-6-phenyl)morpholinyl)-propyl] benzoic acid;
4-[2-(4-(6-(3-Chlorophenyl)-2,3-dimethyl-2-hydroxy)-morpholinyl)propyl]phenoxyacetic acid;
4-[2-(4-(2-(3-Chlorophenyl)-9-hydroxy-5,6,7,8-tetrahydrobenz-(1,4)-oxazinylpropyl]phenoxyacetic acid;
and ester or amide derivatives thereof or pharmaceutically acceptable salts thereof.

5. A pharmaceutical composition comprising a compound of formula (I) as defined in claim 1 or a pharmaceutically acceptable salt thereof, in combination with pharmaceutically acceptable carrier.

6. A method of treating hypoglycaemia in humans or non humans which method comprises administering an effective, non-toxic amount of a compound of formula (I)

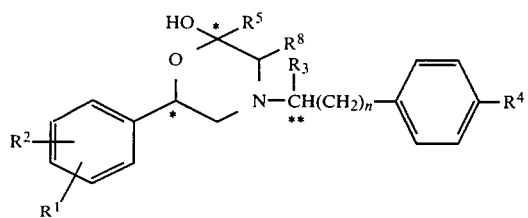 (I)

in which
R$^1$ is hydrogen, halogen, or trifluoromethyl;
R$^2$ is hydrogen or halogen;
R$^3$ is hydrogen or methyl;
R$^4$ is —O(CH$_2$)a CO$_2$H or an ester or amide derivative thereof, O(CH$_2$)$_b$M or —CO$_2$H or an ester or amide derivative thereof
wherein
a is an integer from 1 to 6,
b is an integer from 2 to 7, and
M is hydroxy, C$_{1-6}$ alkoxy or

wherein
R$^6$ and R$^7$ are each hydrogen or C$_{1-6}$ alkyl or

together form a five or six membered ring;
R$^5$ is C$_{1-6}$ alkyl; C$_{1-6}$ alkyl substituted by carboxy or esters and amides thereof; or phenyl optionally substituted by C$_{1-6}$ alkyl, halogen, alkoxy or trifluoromethyl;
R$^8$ is hydrogen or C$_{1-6}$ alkyl or R$^8$ together with R$^5$ form a carbocyclic ring; and
n is 1 or 2,
or a pharmaceutically acceptable salt thereof to a hyperglycaemic human or non-human animal.

7. A method for treating obesity in human or non-human animals, which method comprises administering an effective, non-toxic amount of a compound of formula (I)

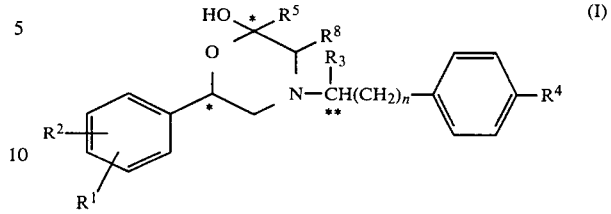 (I)

in which
R$^1$ is hydrogen, halogen, or trifluoromethyl;
R$^2$ is hydrogen or halogen;
R$^3$ is hydrogen or methyl;
R$^4$ is —O(CH$_2$)a CO$_2$H or an ester or amide derivative thereof, O(CH$_2$)$_b$M or —CO$_2$H or an ester or amide derivaive thereof
wherein
a is an integer from 1 to 6,
b is an integer from 2 to 7, and
M is hydroxy, C$_{1-6}$ alkoxy or

wherein
R$^6$ and R$^7$ are each hydrogen or C$_{1-6}$ alkyl or

together form a five or six membered ring;
R$^5$ is C$_{1-6}$ alkyl; C$_{1-6}$ alkyl substituted by carboxy or esters and amides thereof; or phenyl optionally substituted by C$_{1-6}$ alkyl, halogen, alkoxy or trifluoromethyl;
R$^8$ is hydrogen or C$_{1-6}$ alkyl or R$^8$ together with R$^5$ form a carbocyclic ring; and
n is 1 or 2,
or a pharmaceutically acceptable salt thereof to an obese human or non-human animals.

* * * * *